United States Patent [19]

Kowarski

[11] 4,008,717
[45] Feb. 22, 1977

[54] SYSTEM FOR CONTINUOUS WITHDRAWAL AND ANALYSIS OF BLOOD

[75] Inventor: Allen A. Kowarski, Baltimore, Md.

[73] Assignee: The Johns Hopkins University, Baltimore, Md.

[22] Filed: Mar. 5, 1976

[21] Appl. No.: 664,178

Related U.S. Application Data

[60] Continuation-in-part of Ser. No. 587,724, June 17, 1975, which is a division of Ser. No. 323,985, Jan. 15, 1973, Pat. No. 3,908,657.

[52] U.S. Cl. ........................ 128/214 R; 128/278; 128/214.4; 128/218 A; 128/2 F; 128/214 B
[51] Int. Cl.² ...................... A61B 5/00; A61M 1/00
[58] Field of Search ........... 128/214 R, 214 B, 278, 128/334 R, 2 F, 348

[56] References Cited

UNITED STATES PATENTS

| | | | |
|---|---|---|---|
| 2,183,318 | 12/1939 | Burton | 128/214 R |
| 3,425,418 | 2/1969 | Chvapil et al. | 128/334 R |
| 3,496,878 | 2/1970 | Hargest et al. | 128/214 R |
| 3,579,441 | 5/1971 | Brown | 210/23 |
| 3,582,234 | 6/1971 | Isreeli | 417/53 |
| 3,688,317 | 9/1972 | Kurtz | 3/1 |
| 3,701,350 | 7/1970 | Guenther | 128/214 B |
| 3,826,678 | 7/1974 | Hoffman et al. | 428/420 |
| 3,908,657 | 9/1975 | Kowarski | 128/278 |

*Primary Examiner*—Aldrich F. Medbery
*Attorney, Agent, or Firm*—Cushman, Darby & Cushman

[57] ABSTRACT

A small, portable, constant withdrawal device is connected to tubing, including a catheter, whose internal walls are coated with heparin. The catheter is inserted intravenously through a disposal needle into a subject such as a human being. The subject may then move about for a selected period when blood is being slowly withdrawn at a prescribed rate and collected in a container within a housing supporting the device. The collected blood may then be analyzed to permit the measurement of the integrated concentration of glucose, growth hormone or other material in blood. In addition, a portable microdiffusion chamber is incorporated between the indwelling catheter and the extra corporal tubing and is electrically connected through a sensor probe to an associated sensory responsive device. This permits continuous analysis of the withdrawn blood to determine the in vivo concentration of circulating concentrations of materials in the blood.

14 Claims, 8 Drawing Figures

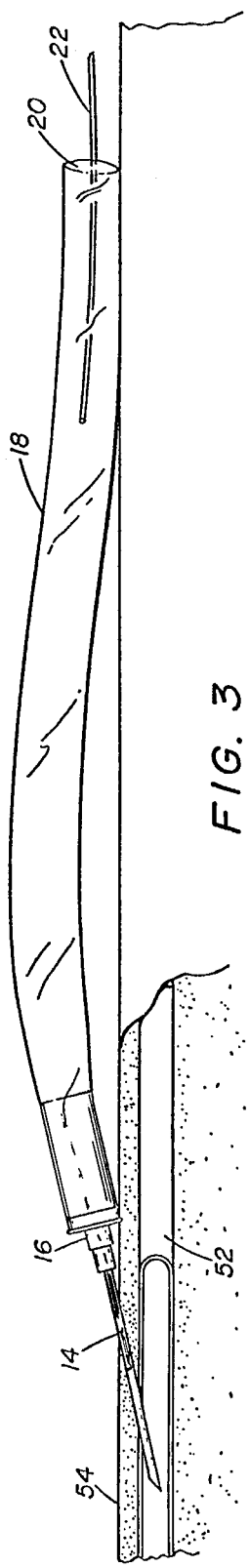
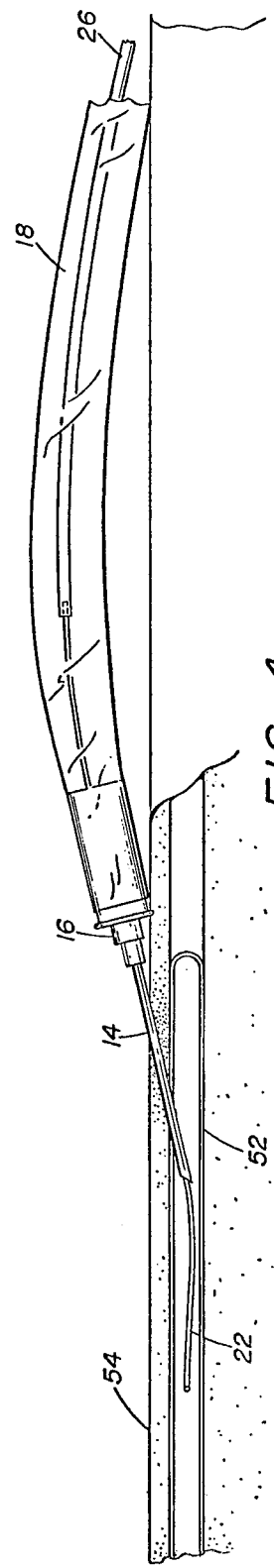
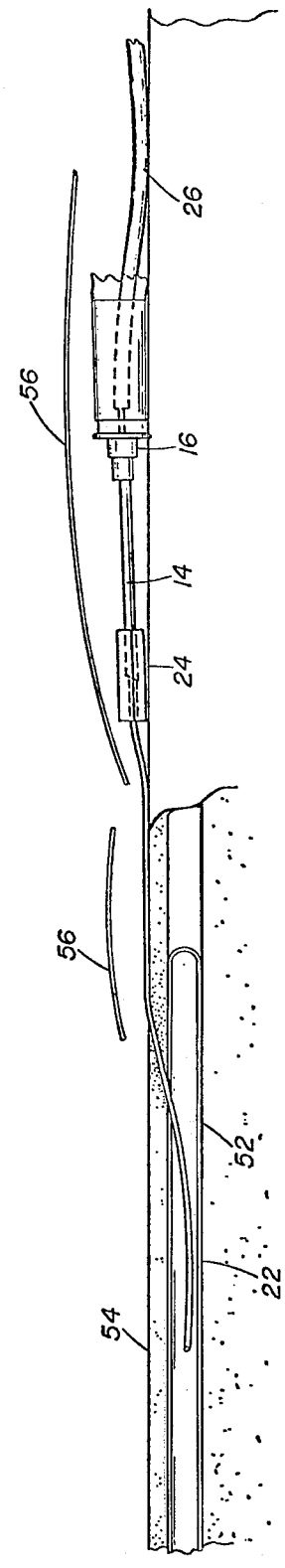
FIG. 3
FIG. 4
FIG. 5

SYSTEM FOR CONTINUOUS WITHDRAWAL AND ANALYSIS OF BLOOD

CROSS-REFERENCE TO RELATED APPLICATION

This application is a continuation-in-part of U.S. Pat. application Ser. No. 587,724, filed on June 17, 1975, which application is a divisional of Ser. No. 323,985 filed Jan. 15, 1973, and now U.S. Pat. No. 3,908,657 issued Sept. 30, 1975.

BACKGROUND AND SUMMARY OF THE INVENTION

This invention relates generally to a system for the continuous withdrawal of blood and more particularly to a system for continuously withdrawing and collecting blood from a subject for a selected period. In order to analyze various properties of materials contained in blood, it is necessary that the blood be withdrawn from the subject. In some instances the blood concentration of material changes rapidly and markedly under physiological and pathological conditions. Values obtained from a single blood specimen, or even multiple blood specimens drawn in quick succession, will not reflect adequately the variations in concentration of the material.

For example, the integration of the concentration curves of hormones has been obtained previously by withdrawing numerous blood samples from a subject, measuring the concentration in each sample, and then calculating the average concentration. Use of this method results in inaccuracies in data collected and calculated as well as resulting in inconvenience and trauma to the subject due to the numerous blood withdrawals.

In an attempt to overcome these disadvantages, complex systems have been developed. For example, in one system, a pump withdraws blood continuously through an indwelling intravenous catheter and infuses by still another pump a heparin solution into the withdrawn blood through a small catheter inserted into an extracorporal portion of the indwelling catheter to prevent clotting in the withdrawal system. Obviously, the indwelling catheter must be larger than the infusion catheter and, therefore, is limited to indwelling in veins of considerable size. Also, two pumps are required and they must be closely synchronized. This and other similar systems require intricate arrangements and types of equipment which result in long periods of immobilization of the subject whose blood is being withdrawn.

Additionally, it is frequently necessary to determine the in vivo concentration of the diffusible fraction of certain materials in the blood. If the blood is withdrawn from the subject to measure, for example, the concentration of the diffusable part of any hormone, drugs or other material in the blood of the subject, the diffusible fraction, which may be 100% thereof, frequently changes once the blood is outside of the body. Therefore, intravenous sensing, rather than the analysis of withdrawn blood, is necessary to obtain accurate results.

In many systems where blood is withdrawn from a subject and conducted through various tubes and component parts of an analyzing system, the tubes and parts can be used only for relatively brief periods without clotting of the blood therein. This reduces the opportunity for long range blood withdrawal and the attendant advantages thereof.

It becomes apparent, then, that a need exists for a non-thrombogenic system for withdrawing blood from a subject over a relatively long period. In addition, there is a need for a non-thrombogenic system for permitting the determination of the in vivo concentration of various materials in blood. Additionally, there is an advantage in the portability of this combined system.

It is, therefore, an object of this invention to provide a system for the withdrawal of blood from a subject over and extended period of time to permit continuous analysis of the blood.

Another object of this invention is to provide a sensing system for permitting the continuous determination of the in vivo concentration of the diffusible fraction of certain materials in the blood as well as the continuous determination of the in vivo concentrations of non-diffusible materials in blood.

Yet another object of this invention is to provide a sensing system for permitting the continuous determination of the in vivo concentration of glucose in the blood.

Still another object of this invention is to provide a non-thrombogenic system which permits the continuous withdrawal of blood through a single catheter over an extended period of time.

Another object of this invention is to provide a non-thrombogenic system which will permit the measurement outside the system of the integrated concentration of a material in blood.

Still another object of this invention is to provide a portable system for the continuous withdrawal of blood from a mobile subject.

Other objects and attendant advantages of this invention will become more readily apparent and understood from the following detailed specification and accompanying drawings.

BRIEF DESCRIPTION OF THE DRAWINGS

FIGS. 3, 4 and 5 are pictorial views showing various steps for inserting a catheter of the system of FIG. 1 into the vein of a subject.

DETAILED DESCRIPTION OF THE INVENTION

Figures 1, 2:
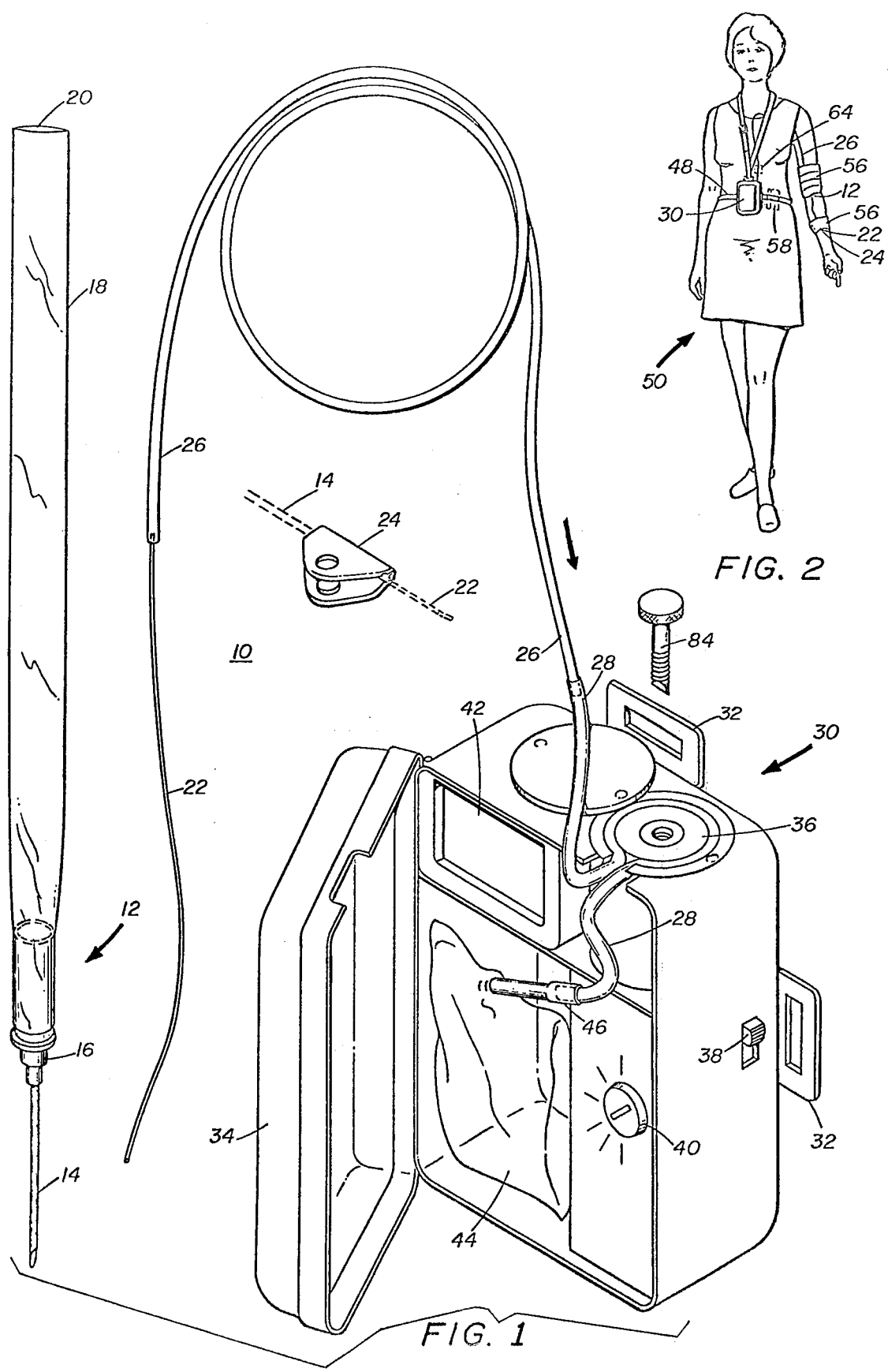
FIG. 1 is a pictorial view showing components of a system for withdrawing blood from a subject.
FIG. 2 is a pictorial view showing the system of FIG. 1 attached to a subject.

Referring now to FIG. 1, a blood withdrawal system 10 includes a disposable needle assembly 12. The needle assembly 12 includes a seventeen gauge needle 14 mounted in a needle hub 16. A plastic sleeve 18 is attached at one end thereof to an extension of the needle hub 16. The other end 20 of the sleeve 18 is open.

The system 10 further includes a nineteen gauge catheter 22 composed of a radiopaque material. The catheter 22 is free at one end and is connected to a plastic tube 26 having a larger diameter which, in turn, is connected at its opposite end to another plastic tube 28 having a still larger diameter. The connected sections of the catheter 22 and tubes 26 and 28 are joined securely by glue.

Thereafter, the internal walls of the catheter 22 and the tubes 26 and 28 are treated to preclude clotting of blood ultimately passing therethrough. This treatment is accomplished in a two-step process. Initially, by using a 50/50 mixture of toluene and petroleum ether, a 5% solution of tridodecylmethyl-ammonium chloride is made. This solution is shaken with 200 milligrams of heparin in 100 milliliters of water. After the emulsion is separated, the supernatant portion of this mixture is drawn into the catheter 22 and tubes 26 and 28 and is left in place for 2 hours. After this, the solution is emptied and filtered, air is drawn through the catheter 22 and tubes 26 and 28 for 24 hours, thus drying the solution that has impregnated the internal walls of the catheter and the tubes. This is accomplished at room temperature. Thereafter, a solution of 200 milligrams of heparin in 50% methyl alcohol and 50% water is drawn through the catheter 22 and tubes 26 and 28 and is left for 3 to 5 hours, withdrawn, and the passageway thereafter air dried by suction for twelve hours as previously described. This impregnation-coating treatment permits a non-thrombogenic use of the catheter 22 and tubes 26 and 28 for at least a 24 hour blood withdrawal period.

Of course, other non-thrombogenic materials besides heparin could be employed for the impregnation, and instead of impregnation, coating is suitable under some circumstances and using some non-thrombogenic materials. Also, synthetic materials that have an anticoagulant (such as heparin) incorporated therein during manufacture, may be utilized for all blood engaging portions of the system.

It is to be noticed that great success has been encountered in coating tubes with very narrow internal diameters due to the drying of the wetted internal surfaces with air sucked through them rather than the conventional method of vacuum oven drying.

A housing 30 is formed having strap holders 32 and a hinged door 34. The housing 30 contains a rotating milking device 36 which functions as a pump or as a means for controlling the rate of withdrawal of blood from a subject 50 (FIG. 2). An on-off switch 38 and a timer-control knob 40 are part of a circuit (not shown) which determines when energy from a battery 42 is applied to the milking device 36. The housing 30 and the various components contained therein are similar to a pump such as a Model ML-6-3 available from Sigmamotor, Inc., of Middleport, N.Y. In the Model ML-6-3, the milking device 36 includes a grooved member into which a flexible tube is positioned. An eccentric roller is rotated at a prescribed rate and engages the flexible tube to milk a fluid in the tube therethrough at a prescribed rate.

The housing 30 is formed with a compartment for containing a plastic bag 44 haing a tubular port 46. An intermediate section of the tube 28 is positioned about the grooved member of the milking device 36 within the housing 30 as illustrated in FIG. 1, and fastened in this position by use of a screw 84. The remaining end of the tube 28 is inserted into the port 46 to facilitate the eventual collection of withdrawn blood. It should be noted that the plastic bag 44 is only representative of a blood collection facility and could include other facilities such as, for example, test tubes. The eccentric wheel of the milking device 36 can then be rotated at a prescribed rate to withdraw blood from the subject 50.

Referring to FIG. 2, straps 48 are used to secure the housing 30 to the subject 50. The tubes 26 and 28 are positioned through the clothing of the subject 50 so that the catheter 22 is positioned along the inside of one arm of the subject.

Referring to FIGS. 3, 4 and 5, a peripheral vein 52 is a lower portion of the arm of the subject 50 is selected and the adjacent skin area 54 is sterilized. The hollow needle 14 is then inserted into the vein 52 as illustrated in FIG. 3. Catheter 22 is disposed with the forward end thereof extending partly into needle 14 and the other end extending through opening 20 of the plastic sleeve 18, the catheter being shown during the inserting operation in FIG. 3.

From the position shown in FIG. 3, the catheter 22 is moved as illustrated in FIG. 4 through the opening of the needle 14 so that the forward end of the catheter is moved into the vein 52. As illustrated in FIG. 5, the needle 14 is withdrawn from the vein 52 and backed over the catheter 22 to the position shown. The removal of the neelde 14 is accomplished in such a manner that the forward end of the catheter 22 remains in the vein 52 of the subject 50.

A plastic clamp 24 (FIGS. 1 and 5) is clamped about the exposed, pointed tip of needle 14 and placed against the skin of the subject 50. Adhesive tape 56 is wrapped about the arm of the subject and the clamp 24 as shown in FIG. 2. The plastic sleeve 18 is then removed from the hub 16 of the needle and adhesive tape 56 is wrapped about the arm of the subject and the needle 14 and the needle hub 16. This permits complete portability of the housing 30 and the contents thereof, the indwelling catheter 22 and tubes 26 and 28. The subject 50 is free to move about and engage in normal movement.

The milking device 36 is operated by selective positioning of the on-off switch 38 and the speed regulator 40. The speed regulator 40 can be set for various speeds of the milking device 36 of the blood withdrawal system 10. For example, the system 10 can be adjusted to continuously and slowly withdraw blood from the subject 50 at a constant rate, e.g., 1 milliliter per hour for 24 hours. Alternatively, the blood can be withdrawn at a rate of 2 milliliters per minute.

The internal heparin treatment of the walls of the catheter 22 and tubes 26 and 28 eliminates any need for heparin infusion into the withdrawn blood and, consequently, for additional pumping and infusion facilities. This enhances the lightweight aspects of the system 10 which improves its portability.

The portability of the system 10 permits normal activity, including sleep, for the subject 50 while the blood is being withdrawn from the subject during the blood-withdrawal period. The blood withdrawn continuously over the extended period of up to 24 hours by use of the system 10 permits analysis of the blood with more accurate results than are attainable with methods where the subject is immobilized or where there are numerous, separate blood withdrawals.

Figure 6:
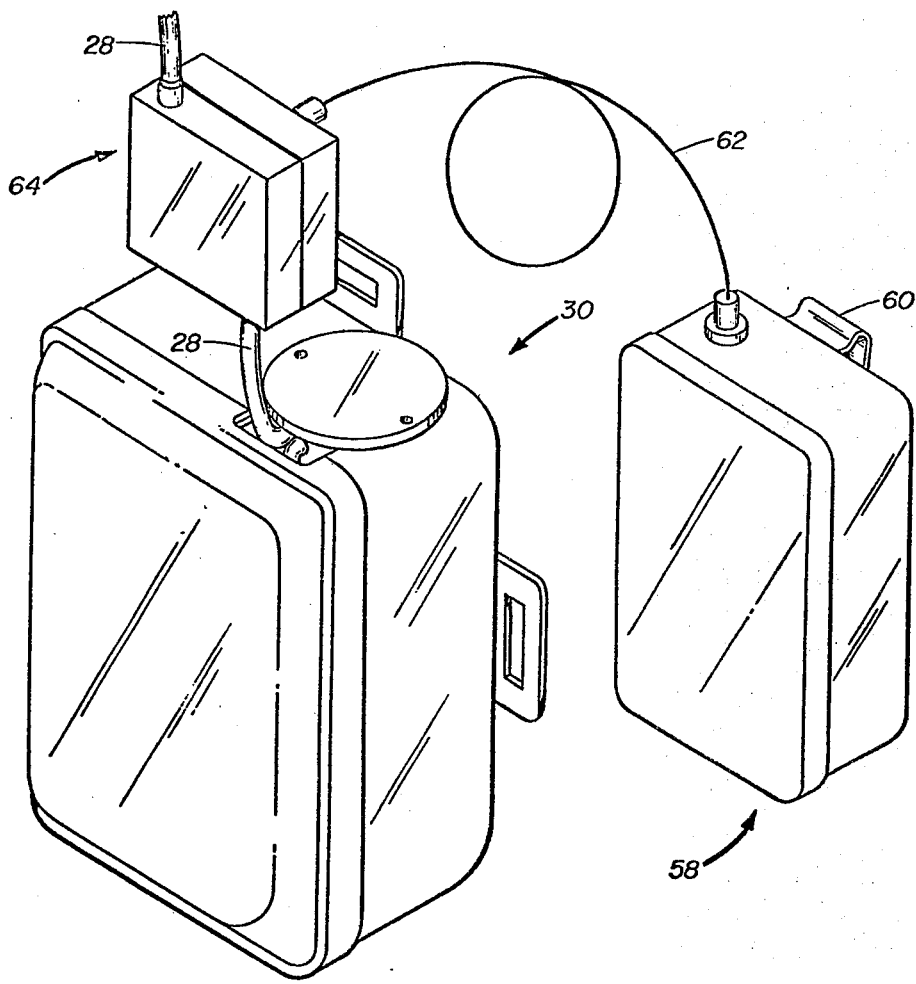
FIG. 6 is a pictorial view showing a sensing system attached to the system of FIG. 1.

Referring to FIG. 6, the system 10 can be modified to include a microdiffusion chamber 64 located between patient 50 and the blood collection facility, e.g., plastic bag 44. A sensor system is used to sense the concentration of diffusible materials in the blood and electrically sends a signal over a wire 62 to a recording device 58. The sensor and the recording device 58 can be, for example, a device available from the Space Science Division of Whitaker Corporation, Waltham, Mass. The recording device 58 is contained within a housing which includes a clip 60 to facilitate the attaching of the housing to the waist strap 48 as illustrated in FIG. 2. This permits portability of the microdiffusion chamber 64 and associated equipment.

Figure 7:
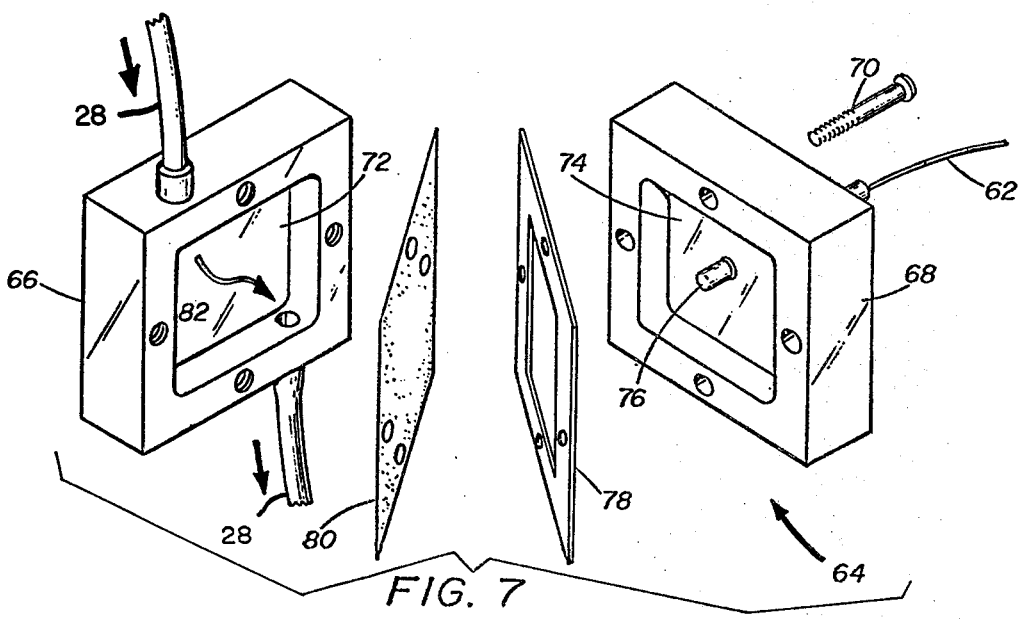
FIG. 7 is an exploded pictorial view of the sensing chamber of the sensing system of FIG. 6.

Referring to FIG. 7, the microdiffusion chamber system 64 includes two plastic housing sections 66 and 68 which are joined together and held by screw fasteners such as fastener 70. The tube 28 is connected to either opening in the chamber 64, liquid flowing from the patient through chamber 66 as shown by arrow 82 and onto the collection device 44. The sections 66 and 68 are formed with chambers 72 and 74, respectively. A sensor probe 76, which is connected to the wire 62, extends into the chamber 74. A sealing gasket 78 and a silicone rubber or cellulose acetate diffusion membrane 80, for example, are positioned between the sections 66 and 68 such that the gasket 78 seals the interface of the two sections and the membrane separates the two chambers 72 and 74. It will be understood that membrane 80 may be made from materials other than silicone rubber or cellulose acetate. Membrane 80 may be porous, containing one or more pores which may vary in size from submicronic to pinhole size. Alternatively, depending on what is being analyzed and the nature of the sensor probe, membrane 80 may be eliminated.

The probe 76 may be the type referred to as a glucose sensor in an article in "Industrial Research" published on Sept. 21, 1972 and appearing on page 27 thereof. It will be understood that probe 76 may alternatively be of the type to detect other diffusible materials in blood, e.g., calcium ion and hydrogen ion. This probe 76 responds by the generation of electrical energy in relation to the concentration of diffusible materials in the blood. Previously, a probe of this type had to be inserted intravenously in order to obtain the electrical impulses necessary for measuring the concentration of diffusible materials in the blood. In the use of the microdiffusion chamber system 64 illustrated in FIGS. 6 and 7, a diluent containing heparin is contained in chamber 74. An example of a suitable diluent would be a buffer solution. As blood passes through the chamber 72, some of the heparin present in chamber 74 will diffuse through the membrane 80 to thereby render the membrane non-thrombogenic. Also, diffusible materials in the blood will diffuse through the membrane 80 into the chamber 74 and will eventually lead to equilibration of the concentration of diffusible materials in the chamber 74 and in venous blood. By use of the sensor probe 76, detection and measurement of the concentration of such materials in the chamber occur and permit the measurement of diffusible materials in vivo. Thus, the sensor probe 76 need not be inserted intravenously of a subject, but can still detect and measure the same properties of the withdrawn blood as if the blood were within the subject. It is also possible to remove the contents of chamber 74 and measure directly the concentration of the diffusible materials therein.

Figure 8:
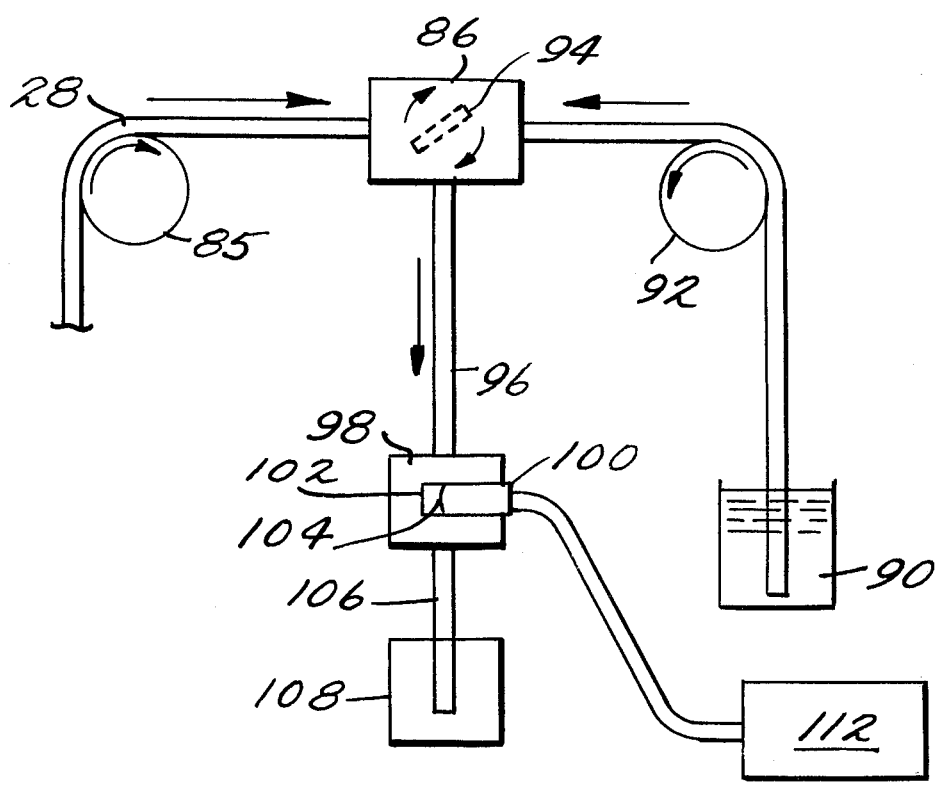
FIG. 8 is a pictorial view of a variation of the sensing system depicted in FIGS. 6 and 7.

FIG. 8 depicts a variation of the sensing system of FIGS. 6 and 7. Tube 28, the internal surface of which has been coated with heparin in accordance with the present method contains blood from a subject which is urged by milking device 85 into mixing chamber 86. The internal surface of mixing chamber 86 may be coated with heparin, but it need not be. Tube 88, one end of which is connected to mixing chamber 86, has its opposite end positioned in reservoir 90. Reservoir 90 contains a diluent, e.g., a buffer solution, which is urged through tube 88 into mixing chamber 86 by milking device 92. The blood and the diluent in mixing chamber 86 are thoroughly mixed by means of a mixing means 94, which may conveniently be a magnetic stirring bar actuated by a magnetic stirrer located outside mixing chamber 86. Mixing device 94 may or may not be coated with heparin.

The blood and diluent mixture flows from mixing chamber 86 through tube 96 into sensing chamber 98. Sensor probe 100 extends into sensing chamber 98. A membrane 102 made of silicone rubber, cellulose acetate or other suitable material is disposed across the tip of sensor probe 100 to form an enclosed cavity 104. Alternatively, a porous membrane containing one or more pores which may conveniently vary in size from submicronic to about pinhole size may be used. An example of such a porous membrane is a Millipore filter. The purpose of membrane 102 in the embodiment depicted in FIG. 8 is to act as a barrier for non-diffusible material, to act as a damper for surges in concentration of the blood-diluent mixture, or both. However, it will be understood that the presence of membrane 102 may not be required in some cases, depending on the nature of the sensor probe and the material in blood which is being analyzed. Cavity 104 contains a diluent which may be, for example, water or a buffer solution. The blood and diluent mixture passes through sensing chamber 98 and is conducted by tube 106 into receiver 108 from which it is ultimately discarded.

It will be understood that, like mixing chamber 86 and mixing device 94, the inner surfaces of tubes 96 and 106 and of sensing chamber 98 as well as the outer surface of sensor probe 100 where it extends into sensing chamber 98 may or may not be coated with heparin in accordance with the present method. If all of the foregoing surfaces which come into contact with the blood-diluent mixture are heparin-coated, only a simple diluent need be present in reservoir 90 for mixing with the blood in mixing chamber 86. Alternatively, if one or more of said surfaces is not coated with heparin, it is necessary that heparin be present in the diluent in reservoir 90 for mixing with the blood in mixing chamber 86. It will be further understood that, if heparin is not present in the blood-diluent mixture or if membrane 102 is not rendered non-thrombogenic with heparin, the diluent present in cavity 104 must contain heparin which diffuses through said membrane to thereby render it non-thrombogenic.

As the blood-diluent mixture, which may or may not contain heparin, passes through sensing chamber 98, the diffusible fraction of materials in the blood diffuses through membrane 102 into cavity 104 and eventually comes into equilibrium with the concentration of said diffusible materials in venous blood. The tip of sensor probe 100 comes into contact with cavity 104 and may, as mentioned above, be of a type to detect glucose, calcium ion, hydrogen ion or other diffusible materials in blood. Sensor probe 100 responds by the generation of electrical energy in relation to the concentration of the diffusible material in blood to which it is sensitive and transmits an electrical signal over wire 110 to recording device 112.

While FIG. 8 depicts sensor probe 100 in sensing chamber 98, it will be understood that probe 100 may alternatively be in mixing chamber 86 or, indeed, at any point downstream from where blood and diluent, and optionally heparin, are mixed. It will be further understood that the blood withdrawal and sensing system of FIG. 8 may be either stationary or portable, i.e., adapted to being strapped to the subject.

While the sensing systems and sensor probes described in FIGS. 7 and 8 are of a type suitable for the analysis of a diffusible material such as glucose, it will be understood that variations of the sensing systems coming within the scope of the claims are anticipated. For example, the membranes 80 and 102 may be eliminated depending on what is being analyzed and the nature of the sensor probes.

In summary, the system 10 permits studies on many aspects of the blood heretofore unobtainable due to inaccuracies which result from previous blood collecting processes and vacillations of substances in the blood. For example, an integrated concentration of substances in the blood is that concentration of a substance determined on a specimen which has been collected over an extended period of time and which represents a mean concentration for a specified period of time. A preferable method, both in respect to scientific accuracy and in reducing trauma to the subject, is to determine an integrated concentration by analyzing the concentration of a sample of blood which results from a uniform collection of blood, minute by minute, over an extended period. The use of the system 10 to collect the blood over an extended period, for example twenty-four hours, permits the practice of the preferable method and thus provides a means of attaining more significant results in blood studies.

A number of hormones and other substances are partially bound to various proteins in blood. The biological activity of these materials is related to the concentration of the unbound moiety rather than to their total concentration. The unbound fraction in vitro is determined by measuring the diffusion fraction. Results obtained by such in vitro methods are of limited usefulness since the studies are conducted outside the body. Also, significant changes in the equilibrium between bound and free fractions occur because of pH changes and other in vitro changes that often are unavoidable. The errors in measuring free concentrations of hormones in vitro may explain a number of inconsistencies between the concentration of the unbound biological materials, measured by presently available methods, and their known biological activity.

The development of the small catheter 22, which will permit the measurements of integrated concentrations of substances, and the development of the small, non-thrombogenic diffusion chamber system 64 as well as the sensing system depicted in FIG. 8, which can be inserted between the catheter 22 and the extracorporal tube 28 in FIG. 6 or tube 106 in FIG. 8, will permit the determination of production rates of various substances which have not previously been determinable and a true, free fraction of the substance under study. The latter is possible because one can expect an equilibrium will be established between the diffusible fraction of materials in blood and the solution contained in the chamber 74 or cavity 104. In this type of study where the blood would constantly come from a vein, the results obtained for the free fraction will better reflect conditions inside the body and give more accurate data regarding interrelationship of hormones and other substances than can currently be determined using crude in vitro techniques.

While the invention has been herein shown and described in what is presently conceived to be the most practical and preferred embodiment thereof, it will be apparent to those of ordinary skill in the art that many modifications may be made thereof within the scope of the invention, which scope is to be accorded the braodest interpretation of the appended claims so as to encompass all equivalent structures and systems.

What is claimed is:

1. A system for continuously withdrawing blood from a subject and determining in vivo concentration of biological materials in the blood, comprising, means insertable into a vein of a subject for providing a passageway for blood being withdrawn from the subject, means engaging only an extra-corporal section of said passageway-providing means for controlling the withdrawing of the blood slowly from the vein at a predetermined constant rate and for a predetermined extended period, means connected to an extra-corporal section of said passageway-providing means for causing diffusion of a diffusible substance of the blood into an amount of diluent, and means for detecting and measuring the concentration of said diffused substance whereby said means responds by the generation of electrical energy in relation to the concentration of the diffused substance, and wherein all blood engaging portions of the system are non-thrombogenic.

2. A system as recited in claim 1, wherein all blood engaging portions of the system are rendered non-thrombogenic by treatment thereof with heparin.

3. A system as recited in claim 1 wherein said diffusion means includes a first chamber means connected in line with said passageway-providing means for permitting the withdrawn blood to pass therethrough, a second chamber means positioned adjacent to said first chamber means, and containing an amount of diluent, each of said first and second chamber means having an open wall, a membrane separating said open walls of said chamber which permits the diffusion of a diffusible substance of the blood into the diluent.

4. A system as recited in claim 3 wherein said detecting and measuring means includes a probe mounted within said second chamber means which responds by the generation of electrical energy in relation to the concentration of a diffused substance, and a recording device electrically connected to said probe for recording the detected and measured energy.

5. A system as recited in claim 1 wherein said system additionally includes a mixing chamber disposed intermediately on said passageway — providing means and adapted to receive blood therefrom, means for feeding diluent into said mixing chamber at a predetermined rate, mixing means located in said mixing chamber for mixing said diluent and said blood together, and wherein all blood engaging portions of the system are non-thrombogenic.

6. A system as recited in claim 5 wherein said means for detecting and measuring the concentration of diffused substance is disposed in a sensing chamber located at a position remote from, but operatively connected to, said mixing chamber.

7. A system as recited in claim 6 wherein said detecting and measuring means includes a probe mounted within said sensing chamber.

8. A system as recited in claim 7 wherein said probe has a tip and wherein a membrane is disposed over said tip to form a cavity defined by said probe tip and said membrane.

9. A system as recited in claim 8 wherein said cavity contains a diluent.

10. A system as recited in claim 9 wherein said means for feeding diluent into said mixing chamber at a predetermined rate comprises a milking device in operative association with a diluent reservoir.

11. A system as recited in claim 10 wherein said mixing means located in said mixing chamber includes a magnetic stirring bar driven by a magnetic stirrer located outside said mixing chamber and magnetically coupled to said magnetic stirring bar.

12. A system as recited in claim 11 wherein all blood engaging portions of said system are non-thrombogenic, being rendered non-thrombogenic by treatment thereof with heparin.

13. A system as recited in claim 1 wherein said system additionally includes a mixing chamber disposed intermediately on said passageway — providing means and adapted to receive blood therefrom, means for feeding diluent into said mixing chamber at a predetermined rate, mixing means located in said mixing chamber for mixing said diluent and said blood together, and wherein said diluent contains a non-thrombogenic material.

14. A system as recited in claim 13 wherein said non-thrombogenic material is heparin.

* * * * *